United States Patent [19]
Danley

[11] Patent Number: 5,509,733
[45] Date of Patent: Apr. 23, 1996

[54] INFRARED HEATED DIFFERENTIAL THERMAL ANALYZER

[75] Inventor: Robert L. Danley, Collingswood, N.J.

[73] Assignee: TA Instruments, Inc., New Castle, Del.

[21] Appl. No.: 171,609

[22] Filed: Dec. 21, 1993

[51] Int. Cl.[6] .................. G01N 25/20; G01N 25/00; G01K 17/00
[52] U.S. Cl. .................................. 374/11; 374/12
[58] Field of Search .................... 374/10, 11, 12

[56] References Cited

U.S. PATENT DOCUMENTS

| | | | |
|---|---|---|---|
| 3,527,081 | 9/1970 | Hill | 374/11 |
| 4,095,453 | 6/1978 | Woo. | |
| 4,126,032 | 11/1978 | Ikeda et al. | 374/10 |
| 4,154,085 | 5/1979 | Hentze | 374/10 |
| 4,214,117 | 7/1980 | Hentze. | |
| 4,248,083 | 3/1981 | Lacy et al.. | |
| 4,304,118 | 12/1981 | Bartha et al. | 374/11 |
| 4,308,008 | 12/1981 | Hentze. | |
| 4,567,849 | 2/1986 | Wan | 374/12 |
| 4,979,896 | 12/1990 | Kinoshita. | |
| 5,098,196 | 3/1992 | O'Neill | 374/11 |
| 5,225,766 | 7/1993 | O'Neill. | |

FOREIGN PATENT DOCUMENTS

| | | | |
|---|---|---|---|
| 0498063 | 8/1992 | European Pat. Off.. | |
| 2704870 | 8/1978 | Germany. | |
| 3511778 | 10/1986 | Germany | 374/12 |
| 0186147 | 11/1982 | Japan | 374/11 |

OTHER PUBLICATIONS

C. Bremer et al., "A Laser Temperature Jump Apparatus Based on Commercial Parts Equipped with Highly Sensitive Spectrophotometric Detection," Measurement Science & Technology, vol. 4, No. 12, Dec. 1993, pp. 1385–1393.
Dworkin et al., "Cooling Device for Low–Temperature Thermal Analysis Studies," Review of Scientific Instruments, 62 (1991) Jun., pp. 1654–1655.
Patent Abstracts of Japan, vol. 8, No. 117, (P–277) (1554) May 31, 1984; JP 59–23240(A), 6 Feb. 1984. (only abstract considered).
N. R. Cox and D. E. McGee, "Use of High Density IR for the Rapid Heating of Metals," Industrial Heating, Apr. 1989, pp. 46–48.
J. A. Hill and C. B. Murphy, "Infrared Heating Applied to Differential Thermal Analysis," Analytical Chemistry, vol. 31, No. 8, Aug. 1959, pp. 1443–1444.
V. D. Hogan and S. Gordon, "Apparatus for Observing Physical Changes at Elevated Temperatures," Analytical Chemistry, vol. 31, No. 8, Aug. 1959, pp. 1443–1444.
Ulvac Sinku–Riko, Inc. product brochure, "7000 Series Thermal Analyzers," 1990, Catalog No. 8411–A12.
Research, Inc. product brochure, "Condensed Catalog for Controls & Infrared Heating," 1991, Catalog No. 1000-B-03-H.

Primary Examiner—Diego F. F. Gutierrez
Attorney, Agent, or Firm—Crowell & Moring

[57] ABSTRACT

The present invention is an infrared-heated differential thermal analyzing instrument. The instrument uses an actively cooled heat sink, and a heat flow restricting element connecting the heat sink to a differential thermal analysis sensor. An IR heater directs IR radiation onto the lateral surfaces of the heat sink and the heat flow restricting element. These lateral surfaces are polished and coated with a high IR reflectance coating, so that heat absorption is minimized. The IR heater preferably uses either elliptical or parabolic mirrors to focus the IR radiation onto the heat sink and the heat flow restricting element. A second embodiment of the invention uses two heat sinks, and two heat flow restricting elements, with one heat sink and one heat flow restricting element mounted on either side of the differential analysis thermal sensor.

22 Claims, 4 Drawing Sheets

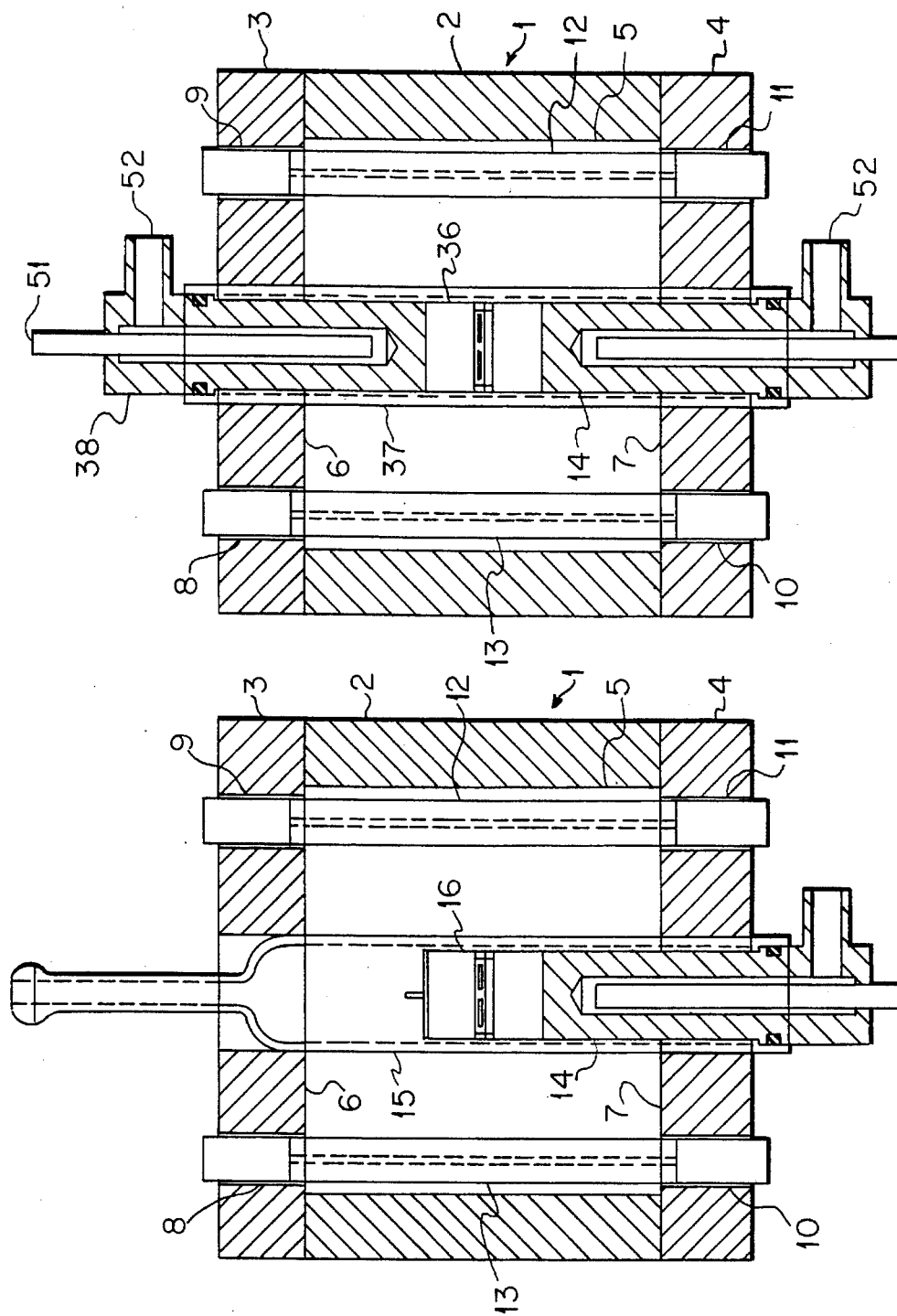

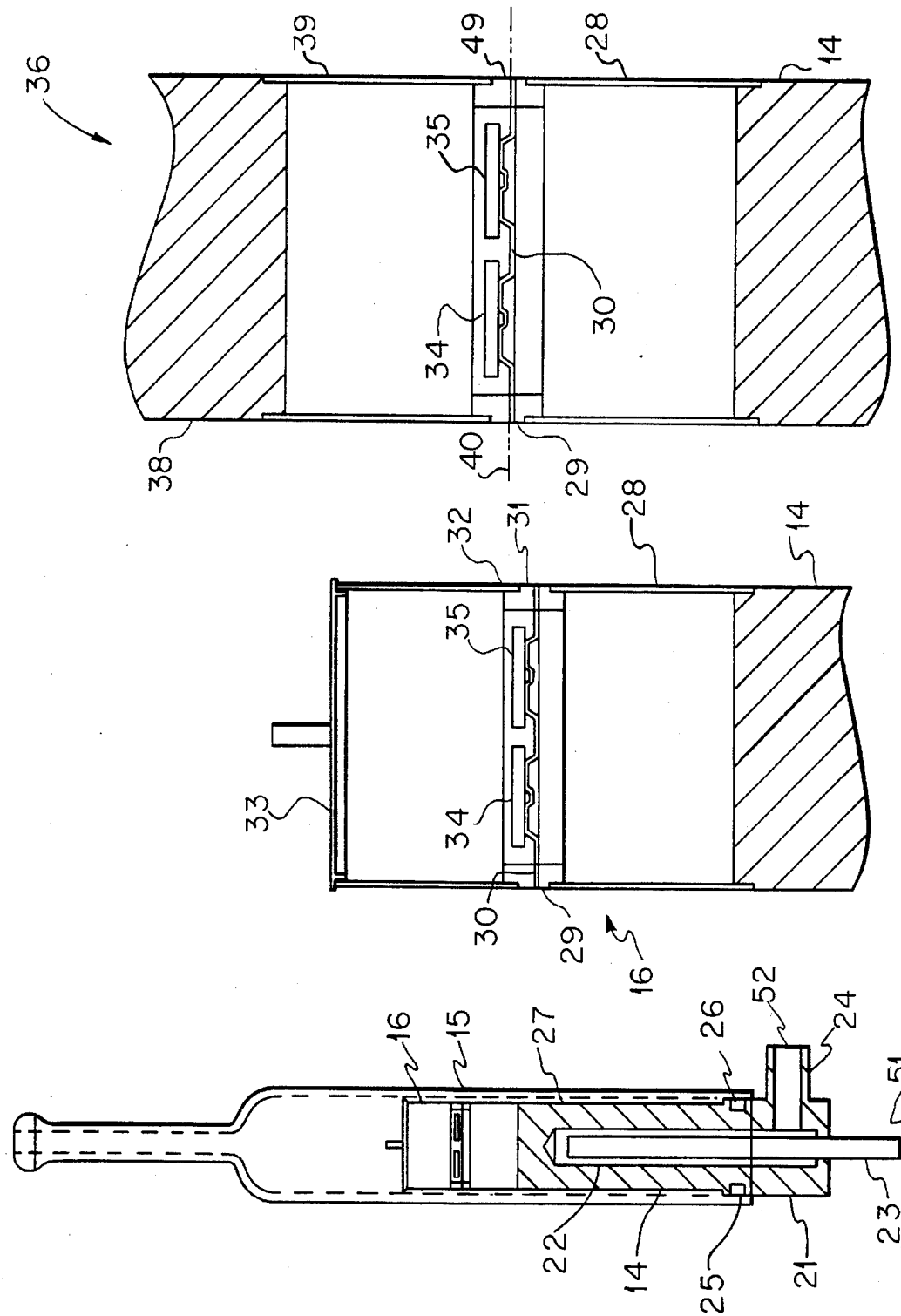

INFRARED HEATED DIFFERENTIAL THERMAL ANALYZER

BACKGROUND

1. Field of the Invention

This invention relates to differential thermal analyzers, such as differential scanning calorimeters, which can be heated and cooled very rapidly.

2. Background of the Invention

Differential thermal analyzers (DTA) measure the difference in temperature between a sample material and a reference material as the sample and reference materials are simultaneously subjected to dynamically controlled changes of temperature. Measurement of the dynamic temperature difference as a function of the sample temperature or of time gives qualitative and quantitative information concerning physical transformations which occur in the sample material. Differential scanning calorimeters (DSCs) are differential thermal analyzers wherein the heat flow to and from the sample material is measured quantitatively.

The heating and cooling rates which can be obtained, and the ability to rapidly equilibrate at a desired temperature are important performance characteristics for differential thermal analyzers. For example, "Isothermal Crystallization," is a measurement of the elapsed time for crystallization of a sample. The experiment consists essentially of heating a material to a temperature above its melting point, and holding it at that temperature until all crystals in the material have melted. The temperature of the sample is then reduced rapidly to a predetermined temperature below the melting point of the crystal and held at that temperature as the material solidifies and crystals grow. The record of differential temperature versus time will show an exothermic peak. That peak records crystallization of the material. The time at which the maximum temperature difference occurs is taken as the crystallization time.

In this measurement, the instrument must reduce the sample temperature from above its melting point to the isothermal temperature as rapidly as possible, and must stabilize the sample temperature at the isothermal temperature very quickly without allowing the sample to cool significantly below the isothermal temperature. Typical specifications for a differential thermal analyzer for isothermal crystallization measurements includes cooling the sample at 200° C./min. and stabilizing the sample temperature at an isothermal temperature in 30 seconds, without undershooting the isothermal temperature by more than 0.5° C.

Differential thermal analyzers include the following major components: (1) holders for the sample and the reference materials, (2) a sensor to measure the temperature difference between the sample and the reference, (3) a sensor to measure the temperature of the sample, and (4) an oven to heat the sample and reference materials.

Most typically, the oven consists of a high conductivity metal block (usually silver) wound with a resistance heating element enclosed in a thermally insulating housing. The oven may also be equipped with a cooling system to remove heat from the oven. The large mass of the oven usually limits the cooling rates to well below the minimum required specification for isothermal crystallization because the cooling system must cool the relatively massive furnace in order to cool the sample. By using cryogenic liquids or multistage mechanical refrigeration cooling systems, conventional differential thermal analyzers have cooling rates up to 50° C./min., over a limited range of temperatures. They usually cannot achieve isothermal temperature stability within the desired time, and with the allowable temperature undershoot. Thus conventional DTA instruments cannot be used satisfactorily for isothermal crystallization measurements.

High density infrared heating uses radiation emitted by infrared (IR) heat lamps to heat the surface of an object. Typically, tubular IR heat lamps are used with either elliptical or parabolic reflectors, which direct and focus the radiation onto the object. The reflectors are usually metallic with a reflective coating having very high specular reflectance in the IR region of the electromagnetic spectrum (i.e., wavelengths between 1 µm and 1 mm). Gold or silver coatings are very effective IR reflective coatings, although gold coatings are generally preferred.

In elliptical reflectors, the IR lamp is positioned at one focus of the ellipse, and the radiant energy emitted by the lamp is focussed by the reflector onto a line located at the opposite focus of the ellipse. In this manner very nearly all of the IR energy emitted by the lamp is concentrated along this focal line, resulting in very high energy densities. By arranging multiple reflectors so that the heated focus of each reflector is collinear, the energy from multiple IR lamps may be focussed along the same line, increasing the energy delivered to the heated focus in proportion to the number of IR lamps and reflectors used.

Parabolic reflectors are used with the IR lamp positioned at the focus of the reflector so that the emitted radiant energy is reflected in parallel rays. Thus, IR heaters employing parabolic reflectors do not deliver the same high energy densities as those having elliptical reflectors, but are well-suited for heating plane surfaces. Multiple parabolic reflector IR heaters may be arranged so that the parallel rays emitted by each assembly intersect, creating a heated region having a large volume. Alternatively, multiple parabolic reflector IR heaters may be arranged to radiate on a surface, thus increasing the energy density at the heated surface.

Because of the very high energy densities attained using IR lamps, very high heating rates can be achieved. Depending on the characteristics of the heated load, especially the load mass, heating rates as high as several thousand ° C. per minute have been achieved.

High density IR heating has been used in thermal analysis instruments, for example, in thermogravimetric analyzers (TGA), differential thermal analyzers (DTA), differential scanning calorimeters (DSC), combined TGA and DTA, and combined TGA and DSC. However, none of these systems have combined an active cooling mechanism with IR heating to achieve the high heating rates, rapid cooling rates and precise temperature control of the present invention.

SUMMARY OF THE INVENTION

The present invention is a differential thermal analyzer which combines high density IR heating with active cooling of the sensing assembly to achieve very high rates of controlled heating and cooling of the differential thermal analysis sensor and the sample being analyzed.

In a first preferred embodiment of the present invention, the differential thermal analyzer includes (1) a differential thermal analysis sensor which can simultaneously measure the temperature of the sample material, and the heat flow to and from the sample, (2) an actively cooled heat sink, (3) a cooling device to supply coolant to the heat sink, (4) a heat flow restricting element connecting the differential thermal analysis sensor to the heat sink, and (5) a high density IR heater incorporating multiple IR heat lamps and elliptical or parabolic reflectors. The high density IR heater assembly is arranged to direct the radiation onto the lateral surfaces of the heat flow restricting element, thereby overcoming the cooling effect of the heat sink, and heating the sensor assembly and the sample. Because the heat sink is also irradiated by the IR heating system, it can absorb large quantities of heat which the cooling system must remove. To reduce this heat load, the lateral surfaces of the heat sink are polished and coated with a high IR reflectance coating so that heat absorption is minimized.

The heat sink coolant supply system may be of the closed loop type wherein the coolant (e.g., water is circulated through the heat sink and through a heat exchanger. Such a system is to be preferred when the operating temperature range is substantially above ambient temperature or where required cooling rates are more modest. A mechanical refrigeration system may be used when the operating temperature range is lower (including sub-ambient temperatures) or where higher cooling rates are needed. The heat sink cooling system may use an expendable liquid cryogen, such as liquid nitrogen, for measurements requiring a very low range of operating temperatures or where the highest cooling rates are required.

There is a trade off between optimizing the heating and cooling rates within a given temperature range. Systems requiring the highest cooling rates will generally have the lowest heating rates, and vice-versa, for a given IR heating assembly. However, an increase in the number of lamps and reflector cavities increases the power delivered to the sensing assembly, so that higher heating rates may be achieved for a given cooling system.

In a second preferred embodiment of the present invention, two heat flow restricting elements and two heat sinks are used. The first heat flow restricting element is connected between the differential thermal analysis sensor and the first heat sink, and the second heat flow restricting element is connected between the differential thermal analysis sensor and the second heat sink. The two heat flow restricting elements and the two heat sinks are located on opposite sides (e.g., above and below) of the differential thermal analysis sensor. The dual heat flow restricting elements and dual heat sinks increase the cooling capacity of the system, thereby making higher cooling rates possible.

Differential thermal analyzers and differential scanning calorimeters constructed in accordance with the present invention can achieve very high heating rates, very rapid cooling rates and very precise temperature control. These instruments are therefore ideal for differential thermal analysis measurements requiring rapid heating and cooling. Such instruments can also be stabilized at a predetermined isothermal temperature very rapidly, with a very small overshoot or undershoot.

Accordingly, it is an object of the present invention to provide differential thermal analyzers and differential scanning calorimeters which can be rapidly heated and cooled.

It is another object of the present invention to provide differential thermal analyzers and differential scanning calorimeters wherein the sample temperature can be rapidly changed to a predetermined temperature, and rapidly stabilized at that temperature.

It is another object of the present invention to increase the accuracy and precision of isothermal crystallization measurements.

These and other objects of the present invention are described in greater detail in the detailed description of the invention, the appended drawings and the attached claims.

BRIEF DESCRIPTION OF THE DRAWINGS

FIG. 1 is a vertical cross section through an assembly having two IR heat lamps, a hi-elliptical reflector, a single heat sink and a single heat flow restricting element.

FIG. 3 is a vertical cross section through the cooling assembly and the sensing assembly.

FIG. 4 is a vertical cross section through the sensing assembly showing the configuration of the differential thermal analysis sensor heat sink and heat flow restricting element.

FIG. 5 is a vertical cross section through an assembly having two IR heat lamps, a bi-elliptical reflector, two heat sinks and two heat flow restricting elements.

FIG. 6 is a vertical cross section through a sensing assembly with two heat flow restricting elements and two heat sinks, showing the configuration of the differential thermal analysis sensor and the heat flow restricting elements.

DETAILED DESCRIPTION OF PREFERRED EMBODIMENTS

Figure 2A:
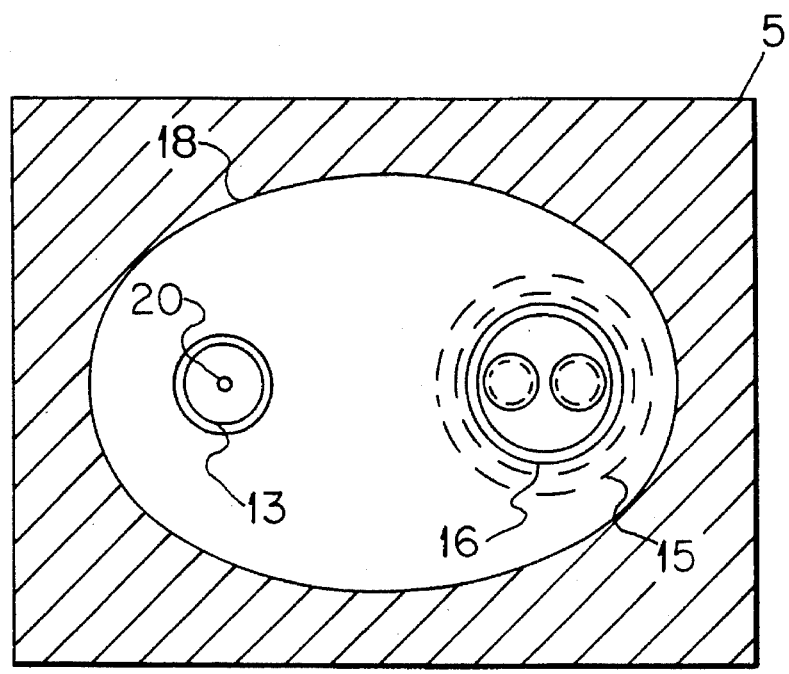
FIG. 2a is a horizontal cross section through an assembly having one IR heat lamp and an elliptical reflector.

FIG. 1 is a vertical cross section of a first preferred embodiment through the plane of the lamp filaments of an IR heated DSC assembly which uses two IR heat lamps, a bi-elliptical reflector, a single heat sink and a single heat flow restricting element. The reflector assembly 1 includes reflector block 2 and end plates 3 and 4. Interior surface 5 of reflector block 2 is a bi-elliptical reflector which is polished to a mirror finish and then coated with gold, which is then also polished to a mirror finish. Gold is preferred over other reflective coatings because, in addition to possessing the requisite spectral reflectance, it does not tarnish. End plates 3 and 4 are flat. Their interior surfaces 6 and 7 are polished to a mirror finish. The surfaces are also coated with gold which is polished to a mirror finish. Holes 8, 9, 10 and 11, through the top and bottom end plates, allow the ends of IR heat lamps 12 and 13 to project through the end plates so that electrical connections (not shown) may be made to the lamps. This protects the vacuum seals of the lamps by allowing the ambient air to cool the seals.

The reflectance of the gold coating in the IR region is less than 100%. Also, the IR lamps emit some radiation at wavelengths outside the range wherein the gold coating has a high reflectance. Because of these two factors, the block and the end plates are heated by absorption of IR radiation, thereby necessitating cooling the block and end plates. Furnace block 2 and end plates 3 and 4 are cooled, preferably by circulation of a coolant such as water through coolant passages (not shown) in the block and the end plates. Alternatively, the block and the end plates can be cooled by cooling fins on the exterior of the block and end plates.

Sensing assembly 16 and heat sink assembly 14 are enclosed by a quartz (vitreous silica) glass enclosure 15 which provides environmental isolation for the sensing assembly 16 and the sample material. Quartz glass is chosen for the enclosure because it has high broadband IR transmittance. IR radiation emitted by the lamps passes through the quartz enclosure tube with a very small absorptive loss. Furthermore, quartz can withstand sustained operation at temperatures as high as 1300° C. It has a low thermal conductivity, reducing heat loss or gain by conduction of heat along the enclosure.

The quartz enclosure allows the region surrounding the sensing assembly to be filled with a protective gas which prevents degradation of the sample during the experimental run, or it may be filled with a gas which reacts with the sample when such conditions are required. For example, oxygen may be used to study the stability of samples under oxidizing conditions. An inlet and an outlet (not shown) are provided to the enclosure so that the desired atmosphere may be introduced and maintained.

FIG. 2a is a cross sectional view of another embodiment of the present invention, which has a single elliptical reflector and a single IR heat lamp, taken transverse to the plane of the IR lamps (just above the plane of the heat flow sensor). The reflecting surface of reflector block 5 is the elliptical cross section cavity 18. Filament 20 of IR lamp 13 is located at one focus of the elliptical reflector cavity 18 and heat flow sensing assembly 16 is located at the other focus of the elliptical reflector. This configuration directs almost all the IR energy emitted by lamp filament 20 onto the surface of the sensing assembly 16, through quartz enclosure 15.

Figure 2B:
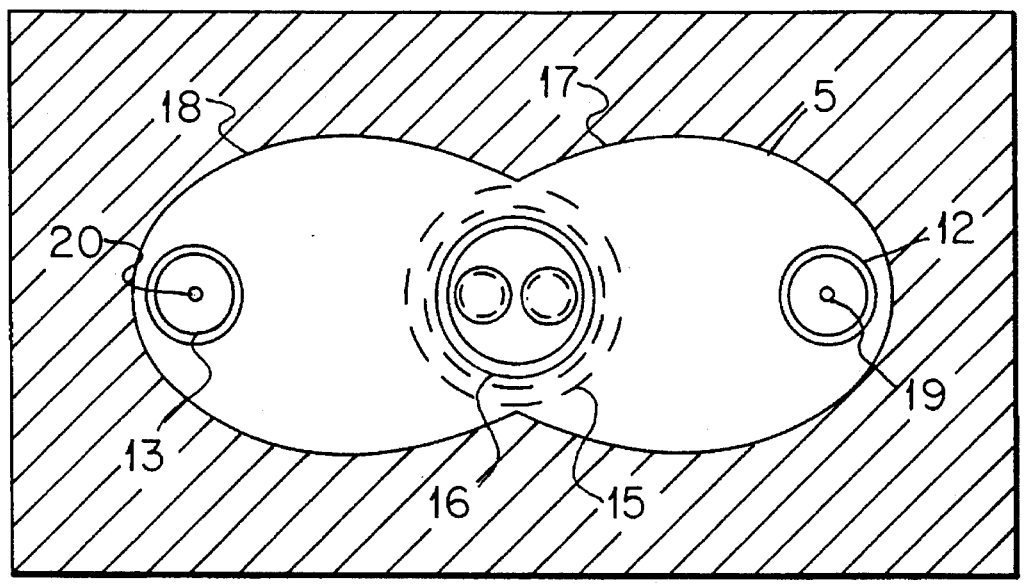
FIG. 2b is a horizontal cross section through an assembly having two IR heat lamps and a bi-elliptical reflector.

FIG. 2b is a cross sectional view of the first preferred embodiment, which has a bi-elliptical reflector, taken transverse to the plane of the IR lamps (just above the plane of the heat flow sensor). Bi-elliptical reflector surface 5 of the reflector block consists of two intersecting elliptical cavities 17 and 18, oriented such that the major axes of the ellipses are collinear, and such that one focus of each ellipse coincides with one focus of the other ellipse. The line defining the coincident foci is the axial centerline for the sensing assembly 16 and the quartz glass enclosure 15. Filament 19 of IR lamp 12 is located at one focus of elliptical reflector cavity 17, while filament 20 of the IR lamp 13 is located at one focus of elliptical reflector cavity 18. Thus, almost all of the IR radiation emitted by lamp filaments 19 and 20 is directed toward the coincident focus of the elliptical reflectors. The IR radiation passes through quartz glass enclosure 15, and heats sensing assembly 16.

Figure 2C:
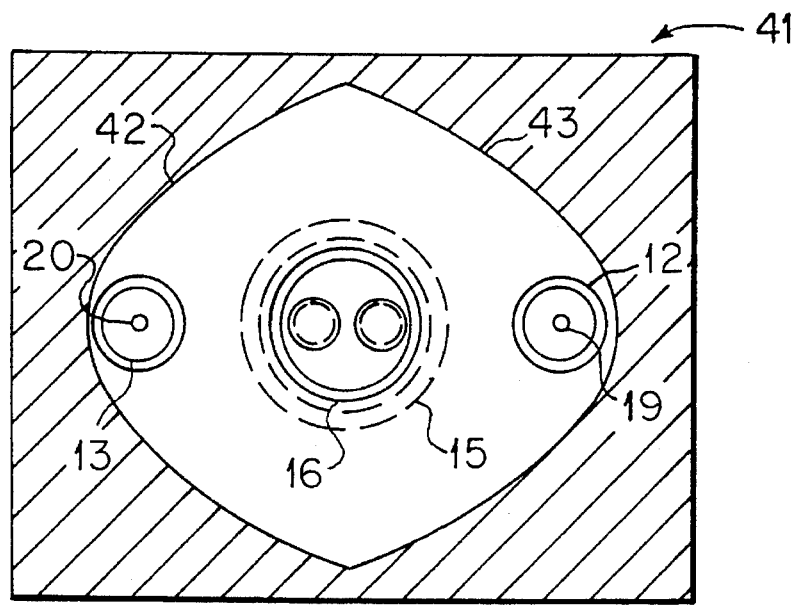
FIG. 2c is a horizontal cross section through an assembly having two IR heat lamps and two parabolic reflectors.

FIG. 2c is a cross sectional view of another embodiment of the present invention, which has two parabolic reflectors and two heat lamps, taken transverse to the plane of the IR lamps (just above the plane of the heat flow sensor). Reflector block 41 includes the parabolic reflector surfaces 42 and 43. The reflectors are arranged so that their axes are collinear. Filament 19 of IR heat lamp 12 is located at the focus of the reflector 43, and filament 20 of IR heat lamp 13 is located at the focus of reflector 42. Heat flow sensing assembly 16 is positioned parallel to the lamp filaments along the reflector axes midway between the lamp filaments. This arrangement directs IR energy emitted from the heat lamps onto the surface of the heat flow sensing assembly, which heats the heat flow sensor assembly. Heat flow sensing assembly 16 is surrounded by quartz glass enclosure 15.

Figure 2D:
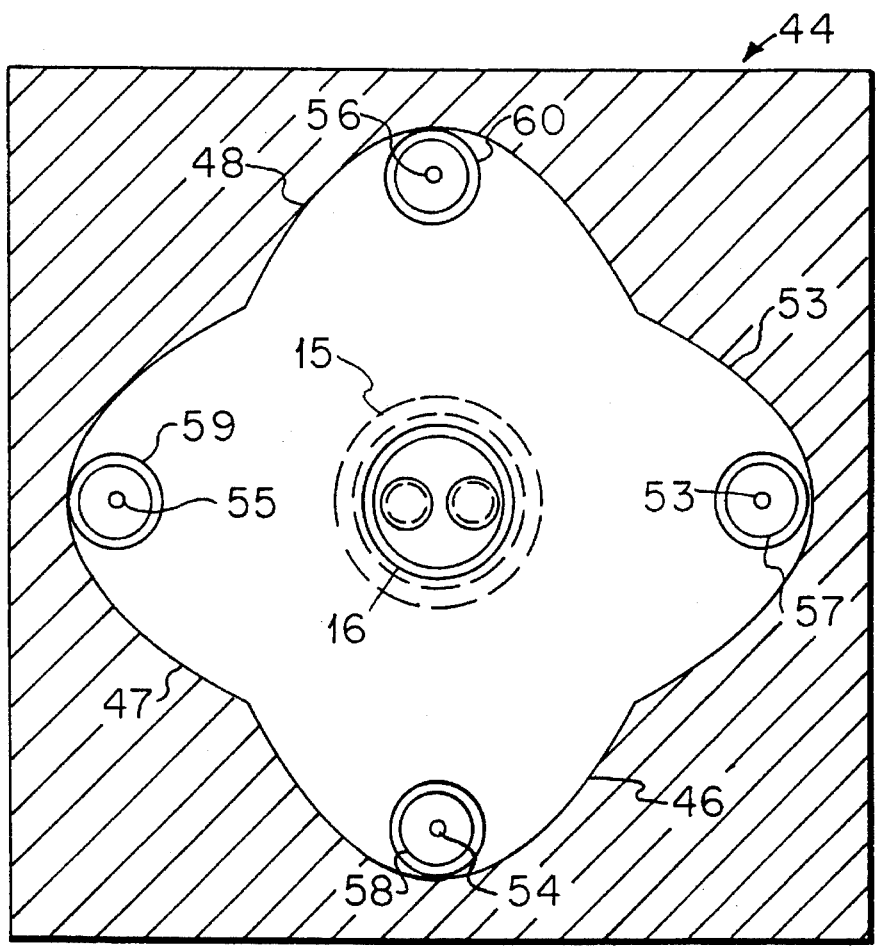
FIG. 2d is a horizontal cross-section through an assembly having four IR heat lamps and four parabolic reflectors.

FIG. 2d is a cross sectional view of another embodiment of the present invention, which has four parabolic reflectors and four heat lamps, taken transverse to the plane of the IR lamps (just above the plane of the heat flow sensor). Reflector block 44 includes the parabolic reflector surfaces 45, 46, 47 and 48. The foci of the four parabolic reflectors are arranged in an equally spaced circular pattern about the centerline of the heat flow sensing assembly 16. The axes of the four parabolic reflectors intersect at the centerline of heat flow sensing assembly 16. The filaments 53, 54, 55, and 56 of the IR lamps 57, 58, 59, and 60 are located at the foci of the four parabolic reflectors. This configuration directs most of the infrared radiation emitted from the four lamps through the quartz enclosure 15 onto the surface of the heat flow sensing assembly 16, thereby heating the heat flow sensing assembly, the samples and the heat flow sensor.

FIG. 3 is a vertical cross section through heat sink assembly 14 and sensing assembly 16 of the first preferred embodiment of the present invention, which has one heat flow restricting element and one heat sink. Heat sink 21 is a cylindrical metal bar with a closed end cooling passage 22. Tube 23 passes upward through the lower end of heat sink 21 into closed end cooling passage 22, terminating just below the end of the passage. Coolant for the heat sink enters the tube 23 via inlet 51, flows upward past the end of the tube and into passage 22, then flows downward inside cooling passage 22, absorbing heat from the heat sink and exiting at discharge tube 24 via coolant outlet 52. O-ring seal 25 in groove 26 at the lower end of the heat sink 21 contacts the inner surface of enclosure 15, sealing the enclosure to heat sink 21, and providing containment of the sample atmosphere. Lateral surface 27 of heat sink 21 is polished to a mirror finish, and coated with gold which is also polished to a mirror finish. The gold coating reduces heating of the heat sink by reflecting almost all of the incident IR radiation away from the surface. Heat flow sensing assembly 16 is surrounded by quartz glass enclosure 15.

FIG. 4 is an enlarged view of the vertical cross section through sensing assembly 16 shown in FIG. 3. The upper end of the heat sink assembly 14 is joined to heat flow restricting element 28, which is joined to temperature equalizing ring 29, which in turn is joined to sensor assembly 30. Sensor assembly 30 is joined to another temperature equalizing ring 31, which is joined to upper sample region enclosure 32. A sample of the material to be analyzed is contained within sample pan 34, while reference pan 35 may be empty or may contain a (generally inert) reference material. All of the joints are made by brazing (or similar joining processes) to ensure complete and continuous joining of all components.

Heat flow restricting element 28 is designed to provide a sufficient path for the flow of heat away from the sensor assembly 30, such that the desired cooling rates may be achieved, but also to have a limited heat conductance, such that the desired maximum temperature and heating rate can be achieved. During operation, the differential temperature across the heat flow restricting element can range from tens or hundreds of degrees Celsius, up to as much as 1,000° C. or more.

The ideal material for heat flow restricting element 28 is a material with a relatively low thermal conductivity, so that its cross section and length are reasonable. Materials with relatively high thermal conductivity would have to have very thin walls and/or be very long to have sufficient thermal resistance. The material should also have relatively low heat capacity so that it does not store large quantities of heat. Because of the very large temperature difference which develops over its length, the heat flow restriction element will be subject to very high stresses due to differential thermal expansion. Generally this requires that the material be fairly ductile, i.e., it will generally limit the material selection to metals. Radiation intercepted by the surface of the sensing assembly is generally not uniformly distributed. It may create an asymmetric temperature distribution in the sensor, which will cause extraneous heat flows during measurements. Such extraneous heat flows may result in deviation of the heat flow signal. These deviations of the baseline signal are highly undesirable.

Temperature equalizing rings 29 and 31 serve to improve the uniformity of temperature about the circumference of the sensor assembly 30 by conduction of heat from higher temperature regions to lower temperature regions, thereby improving the symmetry of the temperature distribution within the sensor, resulting in a baseline heat flow which is very nearly zero over a wide range of temperatures. Temperature equalizing rings 29 and 31 are fabricated from a very high thermal conductivity material, so that heat flows readily in the rings to equalize any temperature non-uniformity. Silver, being the highest thermal conductivity metal, is the preferred material for the temperature equalizing rings when operating temperatures are below 725° C.

The present invention can be used with both differential thermal analyzers and differential scanning calorimeters. The key distinguishing feature of a differential scanning calorimeter from a differential thermal analyzer is simply that the DSC has a baseline heat flow signal which differs very little from zero over a wide range of temperature and which is highly reproducible. This allows the temperature difference signal to be accurately calibrated to give heat flow. A symmetric temperature distribution in the sensor is an essential characteristic of a DSC.

Lid 33 in FIG. 4 covers the sample region. Its sole purpose is to prevent direct heating of the sample and reference pans by the IR radiation. Such extraneous heating would result in heat flow measurement errors.

FIG. 5 is a vertical cross section of a second preferred embodiment of the present invention, which includes an IR heated DSC assembly which uses two heat lamps, a bi-elliptical reflector, two heat sinks and two heat flow restricting elements. The cross section is taken through the plane of the lamp filaments. The second embodiment is similar to the first embodiment, but includes a heat sink assembly 38 above the sensing assembly 36 as well as heat sink assembly 14 below it. Sensing assembly 36 and heat sink assemblies 14 and 38 are contained within a quartz (vitreous silica) glass enclosure 37 which provides environmental isolation for the sensing assembly 36 and hence for the sample material. To facilitate loading and unloading of the sample and reference pans, upper heat sink assembly 38 is removed along with sample enclosure tube 37. The upper heat sink assembly 38 is essentially identical to the lower heat sink assembly and is joined to the upper heat flow restriction element.

FIG. 6 is an enlarged view of the cross section through the sensing assembly shown in FIG. 5. The differential thermal analysis sensor 30 is joined to lower temperature equalizing ring 29, which is joined to lower heat flow restricting element 28, which is joined to lower heat sink 14. Upper temperature equalizing ring 49 is joined to upper heat flow restricting element 39, which is joined to upper heat sink 38. All of the components are joined by brazing or by other similar joining methods. The assembly comprising upper temperature equalizing ring 49, upper heat flow restricting element 39 and upper heat sink 38 separates from the differential thermal analysis sensor 30 along the line 40, allowing access to the sample and reference holders for loading and unloading. Line 40 shows the interface between heat flow sensor 30 and upper temperature equalizing ring 49.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed:

1. A differential thermal analyzer comprising:
   (a) a differential thermal analysis sensor;
   (b) a first actively cooled heat sink;
   (c) a first heat flow restricting element, thermally connecting the first heat sink to the differential thermal analysis sensor;
   (d) a first source of infrared radiation; and
   (e) means for directing the infrared radiation at the heat flow restricting element such that it is incident upon the heat flow restricting element.

2. The differential thermal analyzer of claim 1, wherein the means for directing the infrared radiation reflector.

3. The differential thermal analyzer of claim 2, wherein the reflector is a parabolic reflector.

4. The differential thermal analyzer of claim 2, wherein the reflector is an elliptical reflector.

5. The differential thermal analyzer of claim 2, wherein the reflector is coated with a noble metal.

6. The differential thermal analyzer of claim 5, wherein the noble metal is gold.

7. The differential thermal analyzer of claim 1, further comprising a quartz glass enclosure positioned between the means for directing the infrared radiation and the differential thermal analysis sensor.

8. The differential thermal analyzer of claim 1, further comprising a second source of infrared radiation, wherein the first source of infrared radiation is a first infrared heat lamp having a first filament, and the second source of infrared radiation is a second infrared heat lamp having a second filament.

9. The differential thermal analyzer of claim 8, wherein the means for directing the infrared radiation is a bi-elliptical reflector having a coincident focus, a first focus and a second focus, and wherein the differential thermal analysis sensor and the first heat flow restricting element are located at the coincident focus.

10. The differential thermal analyzer of claim 9, wherein the first filament of the first heat lamp is located at the first focus of the bi-elliptical reflector, and the second filament of the second heat lamp is located at the second focus of the bi-elliptical reflector.

11. The differential thermal analyzer of claim 1, further comprising a second heat sink and a second heat flow restricting element, wherein the differential thermal analysis sensor has a top surface and a bottom surface, and wherein the first heat flow restricting element thermally connects the first heat sink to the bottom surface of the differential thermal analysis sensor, and the second heat flow restricting element thermally connects the second heat sink to the top surface of the differential thermal analysis sensor.

12. The differential thermal analyzer of claim 11, further comprising a second source of infrared radiation, wherein the first source of infrared radiation is a first infrared heat lamp having a first filament, and the second source of infrared radiation is a second infrared heat lamp having a second filament.

13. The differential thermal analyzer of claim 12, wherein the means for directing the infrared radiation is a bi-elliptical reflector having a coincident focus, a first focus and a second focus, and wherein the differential thermal analysis sensor, the first heat flow restricting element, and the second heat flow restricting element are located at the coincident focus.

14. The differential thermal analyzer of claim 13, wherein the first filament of the first heat lamp is located at the first focus of the bi-elliptical reflector, and the second filament of the second heat lamp is located at the second focus of the bi-elliptical reflector.

15. The differential thermal analyzer of claim 1, wherein the means for directing the infrared radiation is a plurality of parabolic reflectors, and wherein the first source of infrared radiation comprises a plurality of heat lamps, each heat lamp emitting infrared rays, with one heat lamp positioned at the focus of each parabolic reflector, wherein the number of units in the plurality of heat lamps is equal to the number of units in the plurality of parabolic reflectors.

16. The differential thermal analyzer of claim 15, wherein the parabolic reflectors are oriented such that the infrared rays reflected by the parabolic reflectors intersect, creating a heated region.

17. The differential thermal analyzer of claim 16, wherein the differential thermal analysis sensor and the first heat flow restricting element are positioned within the heated region.

18. The differential thermal analyzer of claim 1, wherein the means for directing the infrared radiation is a plurality of elliptical reflectors, each reflector having two focusses, and wherein the first source of infrared radiation comprises a plurality of heat lamps, each heat lamp emitting infrared rays, with one heat lamp positioned at one focus of each elliptical reflector, wherein the number of units in the plurality of heat lamps is equal to the number of units in the plurality of elliptical reflectors.

19. A differential thermal analyzer comprising:

(a) a differential thermal analysis sensor;

(b) a first actively cooled heat sink and a second actively cooled heat sink;

(c) a first heat flow restricting element, thermally connecting the first heat sink to the differential thermal analysis sensor and a second heat flow restricting element, thermally connecting the second heat sink to the differential thermal analysis sensor;

(d) a source of infrared radiation; and (e) means for directing the infrared radiation at the heat flow restricting elements such that it is incident upon the heat flow restricting elements.

20. The differential thermal analyzer of claim 19, wherein the source of infrared radiation is a plurality of infrared heat lamps.

21. The differential thermal analyzer of claim 20:

wherein the means for directing the infrared radiation is a multi-elliptical reflector having a coincident focus, having a plurality of elliptical reflecting surfaces, and having a plurality of focusses, wherein the number of units in the plurality of elliptical reflecting surfaces and the number of units in the plurality of focusses are equal to the number of units in the plurality of infrared heat lamps;

wherein each infrared heat lamp is located at one focus of one elliptical reflecting surface such that each elliptical reflecting surface has one infrared heat lamp at one focus; and wherein the differential thermal analysis sensor and the first and second heat flow restricting elements are located at the coincident focus.

22. The differential thermal analyzer of claim 20:

wherein the means for directing the infrared radiation is a multiparabolic reflector having a plurality of parabolic reflecting surfaces and a plurality of focusses, the number of units in the plurality of parabolic reflecting surfaces and the number of units in the plurality of focusses being equal to the number of units in the plurality of infrared heat lamps, wherein each infrared heat lamp is located at one focus of each parabolic reflecting surface such that each elliptical reflecting surface has one infrared heat lamp at one focus, and such that the infrared radiation is reflected from each parabolic surface in parallel rays, said parabolic reflecting surfaces being oriented such that the parallel rays reflected by each parabolic reflecting surface intersect, creating a heated region; and wherein the differential thermal analysis sensor and the first and second heat flow restricting elements are located within the heated region.

* * * * *